(12) United States Patent
Yamamoto et al.

(10) Patent No.: US 11,857,366 B2
(45) Date of Patent: Jan. 2, 2024

(54) ULTRASONOGRAPHY SYSTEM

(71) Applicant: FUJIFILM Corporation, Tokyo (JP)

(72) Inventors: Katsuya Yamamoto, Ashigarakami-gun (JP); Yasuhiko Morimoto, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 17/381,332

(22) Filed: Jul. 21, 2021

(65) Prior Publication Data
US 2022/0071592 A1    Mar. 10, 2022

(30) Foreign Application Priority Data

Sep. 8, 2020    (JP) ................................ 2020-150289

(51) Int. Cl.
*A61B 8/00*      (2006.01)
*A61B 8/12*      (2006.01)

(52) U.S. Cl.
CPC ................ *A61B 8/445* (2013.01); *A61B 8/12* (2013.01); *A61B 8/4488* (2013.01); *A61B 8/56* (2013.01)

(58) Field of Classification Search
CPC ......... A61B 8/445; A61B 8/12; A61B 8/4488; A61B 8/56; A61B 8/4483
See application file for complete search history.

(56) References Cited

U.S. PATENT DOCUMENTS

| 5,834,699 | A | 11/1998 | Buck et al. | |
|---|---|---|---|---|
| 6,628,975 | B1 * | 9/2003 | Fein | A61B 5/1495 600/323 |
| 2002/0010901 | A1 * | 1/2002 | Otaguro | G06F 30/367 716/104 |
| 2002/0139562 | A1 | 10/2002 | Daane et al. | |

(Continued)

FOREIGN PATENT DOCUMENTS

| JP | 61-293438 A | 12/1986 |
|---|---|---|
| JP | 3-80841 A | 4/1991 |

(Continued)

OTHER PUBLICATIONS

Japanese Office Action for corresponding Japanese Application No. 2020-150289, dated Apr. 4, 2023, with English translation.

*Primary Examiner* — Oommen Jacob
(74) *Attorney, Agent, or Firm* — Birch, Stewart, Kolasch & Birch, LLP

(57) ABSTRACT

Provided is an ultrasonography system capable of suppressing image quality deterioration of an ultrasound image and achieving reduction in diameter of an ultrasound endoscope. An ultrasonography system includes an ultrasound transducer array in which ultrasound transducers are arranged, a cable that is connected to the ultrasound transducers, the cable having a non-coaxial cable that includes a first cable bundle consisting of signal wires and ground wires, and a first shield layer with which the first cable bundle is coated, and an outer coat with which a second cable bundle consisting of a plurality of the non-coaxial cables is coated, a (Continued)

memory that stores static capacitance data indicating static capacitance of each signal wire included in the first cable bundle, and a processor that periodically corrects transmission and reception sensitivity of each ultrasound transducer based on the static capacitance data stored in the memory.

7 Claims, 12 Drawing Sheets

(56) References Cited

U.S. PATENT DOCUMENTS

| | | | | |
|---|---|---|---|---|
| 2005/0050491 | A1* | 3/2005 | Keller | G06F 30/367 716/115 |
| 2005/0183049 | A1* | 8/2005 | Ohba | G06F 30/367 716/112 |
| 2006/0241479 | A1* | 10/2006 | Wada | A61B 8/12 600/466 |
| 2007/0106966 | A1* | 5/2007 | Inoue | G06F 30/398 716/136 |
| 2008/0045838 | A1* | 2/2008 | Hyuga | G01S 15/8927 600/463 |
| 2009/0251025 | A1* | 10/2009 | Kondou | G01N 29/2406 310/336 |
| 2010/0049054 | A1* | 2/2010 | Sawada | G10K 11/02 600/466 |
| 2010/0274136 | A1* | 10/2010 | Cerofolini | B06B 1/0622 600/459 |
| 2012/0136599 | A1* | 5/2012 | Inui | G06F 30/367 702/65 |
| 2012/0271172 | A1* | 10/2012 | Komuro | B06B 1/0215 600/441 |
| 2013/0341065 | A1 | 12/2013 | Sato et al. | |
| 2015/0268091 | A1* | 9/2015 | Abe | A61B 8/56 367/181 |
| 2018/0247740 | A1* | 8/2018 | Khamphilavong | A61B 8/4427 |
| 2019/0090857 | A1* | 3/2019 | Yamamoto | A61B 8/4444 |
| 2019/0239854 | A1* | 8/2019 | Okada | G01S 7/5205 |
| 2020/0205777 | A1* | 7/2020 | Kumata | A61B 8/12 |
| 2023/0000471 | A1 | 1/2023 | Yamamoto et al. | |

FOREIGN PATENT DOCUMENTS

| | | |
|---|---|---|
| JP | 8-308830 A | 11/1996 |
| JP | 9-231837 A | 9/1997 |
| JP | 11-162268 A | 6/1999 |
| JP | 2006-81764 A | 3/2006 |
| JP | 2006-247025 A | 9/2006 |
| JP | 2008-93314 A | 4/2008 |
| JP | 2010-232182 A | 10/2010 |
| JP | 2014-29846 A | 2/2014 |
| JP | 2015-177907 A | 10/2015 |
| JP | 2019-54962 A | 4/2019 |
| JP | 2020-625 A | 1/2020 |
| WO | WO 2007/055320 A1 | 5/2007 |
| WO | WO 2016/143133 A1 | 9/2016 |

* cited by examiner

ULTRASONOGRAPHY SYSTEM

CROSS-REFERENCE TO RELATED APPLICATIONS

The present application claims priority under 35 U.S.C § 119 to Japanese Patent Application No. 2020-150289 filed on Sep. 8, 2020. The above application is hereby expressly incorporated by reference, in its entirety, into the present application.

BACKGROUND OF THE INVENTION

1. Field of the Invention

The present invention relates to an ultrasonography system.

2. Description of the Related Art

In recent years, an ultrasonography system that observes a state inside a body of a subject by irradiating the inside of the body with ultrasonic waves and receives reflected waves to capture video has been used in medical practice.

For example, as disclosed in JP2019-054962A, such an ultrasonography system comprises an ultrasound endoscope comprising a distal end part that comprises piezoelectric elements configuring ultrasound transducers, a bending part and a flexible part connected to a proximal end of the distal end part, a plurality of coaxial cables that are inserted into the bending part and the flexible part, and a wiring substrate that electrically connects the piezoelectric elements and the coaxial cables, and a processor that is electrically connected to the piezoelectric elements and transmits and receives electric signals to and from the piezoelectric elements.

SUMMARY OF THE INVENTION

Incidentally, a coaxial cable is configured by covering the periphery of one signal wire coated for insulation with a shield layer and an outer coat. For this reason, the outer diameter of the coaxial cable increases, and the ultrasound endoscope is hardly reduced in diameter.

Accordingly, a case where an ultrasound endoscope is reduced in diameter by applying a non-coaxial cable instead of the coaxial cable is considered. However, in the non-coaxial cable, a difference in static capacitance between a plurality of signal wires is likely to occur. The difference in static capacitance results in a difference in sensitivity, and there may be an influence on sensitivity variation between the ultrasound transducers, and as a result, on an image.

The invention has been accomplished in view of such a situation, and an object of the invention is to provide ultrasonography system capable of suppressing image quality deterioration of an ultrasound image and achieving reduction in diameter of an ultrasound endoscope.

An ultrasonography system of a first aspect comprises an ultrasound transducer array in which a plurality of ultrasound transducers are arranged, a cable that is connected to the plurality of ultrasound transducers, the cable having a non-coaxial cable that includes a first cable bundle consisting of a plurality of signal wires and a plurality of ground wires, and a first shield layer with which the first cable bundle is coated, and an outer coat with which a second cable bundle consisting of a plurality of the non-coaxial cables is coated, a memory that stores static capacitance data indicating static capacitance of each signal wire included in the first cable bundle, and a processor that periodically corrects transmission and reception sensitivity of each ultrasound transducer based on the static capacitance data stored in the memory.

In an ultrasonography system of a second aspect, the memory stores sensitivity data indicating sensitivity of each ultrasound transducer, and the processor periodically corrects the transmission and reception sensitivity of each ultrasound transducer based on the static capacitance data and the sensitivity data stored in the memory.

In an ultrasonography system of a third aspect, the processor drives the ultrasound transducer connected to the signal wire having high static capacitance with a transmission signal having a higher voltage than the ultrasound transducer connected to the signal wire having low static capacitance.

In an ultrasonography system of a fourth aspect, the processor applies a higher gain value to a reception signal from the ultrasound transducer connected to the signal wire having high static capacitance than a reception signal from the ultrasound transducer connected to the signal wire having low static capacitance.

In an ultrasonography system of a fifth aspect, the processor applies a higher attenuation value to a reception signal from the ultrasound transducer connected to the signal wire having low static capacitance than a reception signal from the ultrasound transducer connected to the signal wire having high static capacitance.

In an ultrasonography system of a sixth aspect, in the ultrasound transducer array, the ultrasound transducer connected to the signal wire having low static capacitance is disposed on a center side, and the ultrasound transducer connected to the signal wire having high static capacitance is disposed on an end portion side.

In an ultrasonography system of a seventh aspect, the processor sets a difference in static capacitance between the signal wires included in each first cable bundle to be equal to or less than 2 dB.

With the ultrasonography system of the invention, it is possible to suppress image quality deterioration of an ultrasound image and to achieve reduction in diameter of an ultrasound endoscope.

DESCRIPTION OF THE PREFERRED EMBODIMENTS

Hereinafter, a preferred embodiment of an ultrasound endoscope according to the invention will be described referring to the accompanying drawings.

Figure 1:
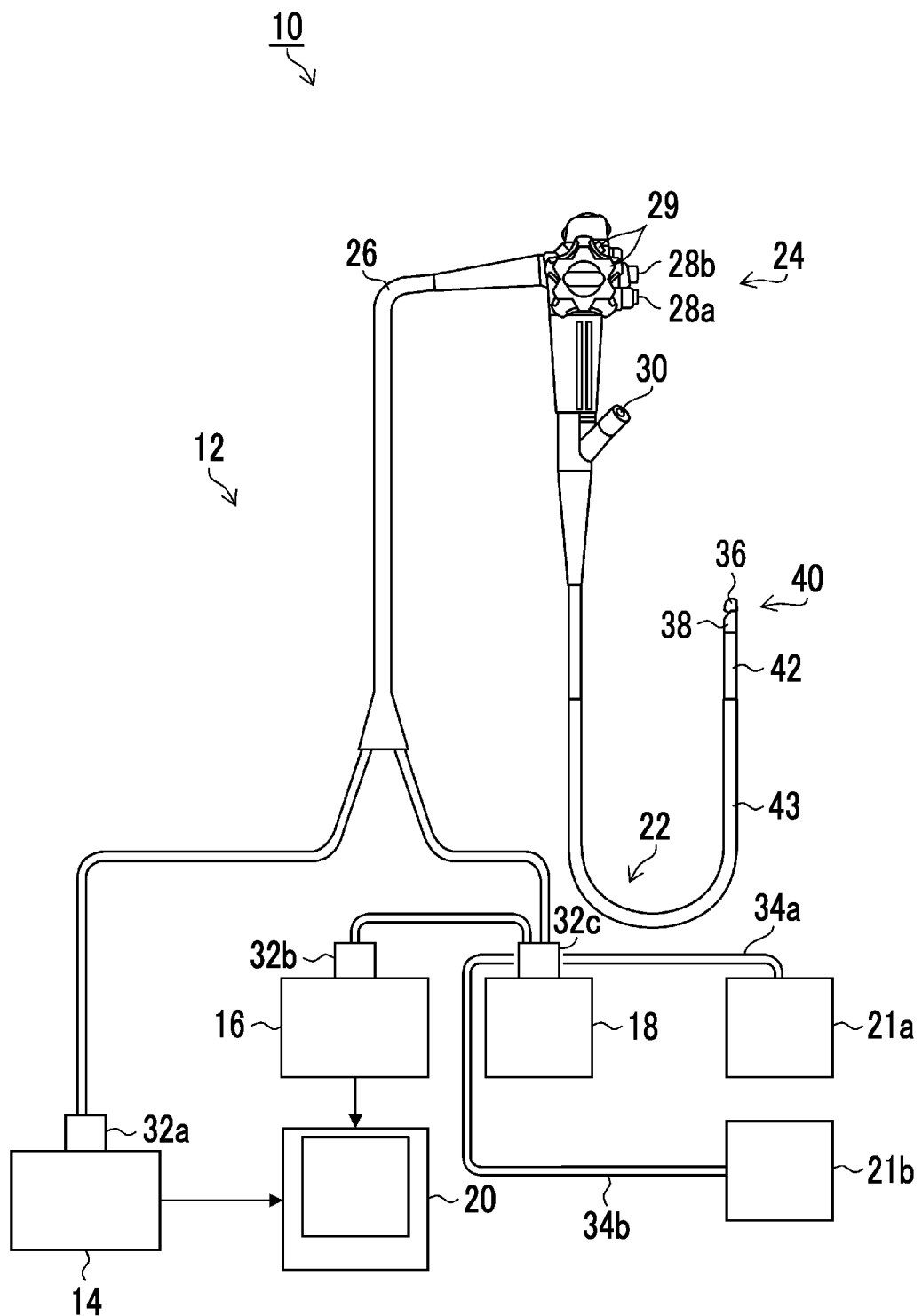
FIG. 1 is a schematic configuration diagram showing an example of the configuration of an ultrasonography system.

FIG. 1 is a schematic configuration diagram showing an example of an ultrasonography system 10 that uses an ultrasound endoscope 12 of an embodiment.

As shown in FIG. 1, the ultrasonography system 10 comprises the ultrasound endoscope 12, an ultrasound processor device 14 that generates an ultrasound image, an endoscope processor device 16 that generates an endoscope image, a light source device 18 that supplies illumination light, with which the inside of a body cavity is illuminated, to the ultrasound endoscope 12, and a monitor 20 that displays the ultrasound image and the endoscope image. The ultrasonography system 10 comprises a water supply tank 21a that stores cleaning water or the like, and a suction pump 21b that sucks aspirates inside the body cavity.

The ultrasound endoscope 12 has an insertion part 22 that is inserted into the body cavity of the subject, an operating part 24 that is consecutively provided in a proximal end portion of the insertion part 22 and is used by an operator to perform an operation, and a universal cord 26 that has one end connected to the operating part 24.

In the operating part 24, an air and water supply button 28a that opens and closes an air and water supply pipe line (not shown) from the water supply tank 21a, and a suction button 28b that opens and closes a suction pipe line (not shown) from the suction pump 21b are provided side by side. In the operating part 24, a pair of angle knobs 29 and 29 and a treatment tool insertion port 30 are provided.

In the other end portion of the universal cord 26, an ultrasound connector 32a that is connected to the ultrasound processor device 14, an endoscope connector 32b that is connected to the endoscope processor device 16, and a light source connector 32c that is connected to the light source device 18 are provided. The ultrasound endoscope 12 is attachably and detachably connected to the ultrasound processor device 14, the endoscope processor device 16, and the light source device 18 respectively through the connectors 32a, 32b, and 32c. The connector 32c comprises an air and water supply tube 34a that is connected to the water supply tank 21a, and a suction tube 34b that is connected to the suction pump 21b.

The insertion part 22 has, in order from a distal end side, a distal end part 40 that has an ultrasound observation part 36 and an endoscope observation part 38, a bending part 42 that is consecutively provided on a proximal end side of the distal end part 40, and a flexible part 43 that couples a proximal end side of the bending part 42 and the distal end side of the operating part 24.

The bending part 42 is remotely bent and operated by rotationally moving and operating a pair of angle knobs 29 and 29 provided in the operating part 24. With this, the distal end part 40 can be directed in a desired direction.

The ultrasound processor device 14 generates and supplies an ultrasound signal for making an ultrasound transducer array 50 of an ultrasound transducer unit 46 (see FIG. 2) of the ultrasound observation part 36 described below generate an ultrasonic wave. The ultrasound processor device 14 receives and acquires an echo signal reflected from an observation target part irradiated with the ultrasonic wave, by the ultrasound transducer array 50 and executes various kinds of signal processing on the acquired echo signal to generate an ultrasound image that is displayed on the monitor 20.

The endoscope processor device 16 receives and acquires a captured image signal acquired from the observation target part illuminated with illumination light from the light source device 18 in the endoscope observation part 38 and execute various kinds of signal processing and image processing on the acquired image signal to generate an endoscope image that is displayed on the monitor 20.

The ultrasound processor device 14 and the endoscope processor device 16 are configured with two devices (computers) provided separately. Note that the invention is not limited thereto, and both the ultrasound processor device 14 and the endoscope processor device 16 may be configured with one device.

To image an observation target part inside a body cavity using the endoscope observation part 38 to acquire an image signal, the light source device 18 generates illumination light, such as white light including light of three primary colors of red light, green light, and blue light or light of a specific wavelength. Light propagates through a light guide (not shown) and the like in the ultrasound endoscope 12, and is emitted from the endoscope observation part 38, and the observation target part inside the body cavity is illuminated with light.

The monitor 20 receives video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously.

In the embodiment, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with the operator.

Next, the configuration of the distal end part 40 will be described referring to FIGS. 2 to 4.

Figure 2:
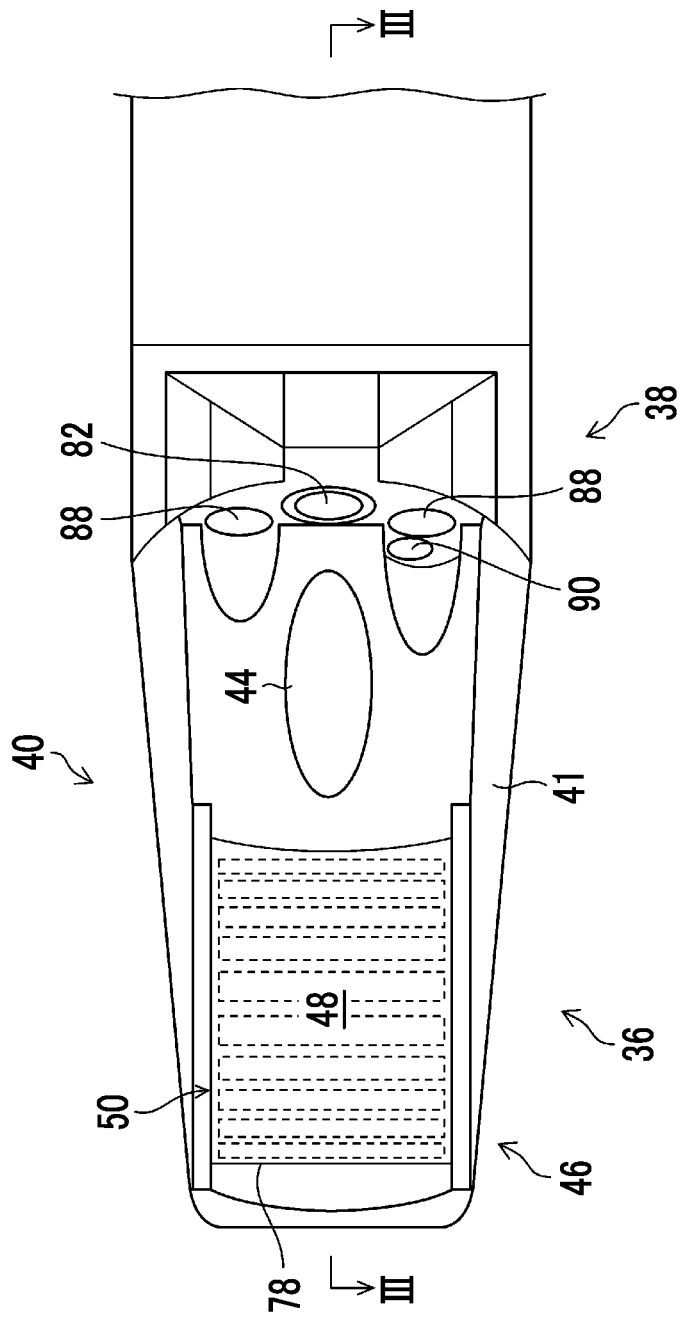
FIG. 2 is a partial enlarged plan view showing a distal end part of an ultrasound endoscope of FIG. 1 and the vicinity of the distal end part.

FIG. 2 is a partial enlarged plan view showing the distal end part 40 shown in FIG. 1 and the vicinity thereof the distal end part 40. FIG. 3 is a cross-sectional view taken along the line shown in FIG. 2, and is a longitudinal sectional view of the distal end part 40 taken along a center line thereof in a longitudinal axis direction. FIG. 4 is a cross-sectional view taken along the line IV-IV shown in FIG. 3, and is a cross-sectional view of the ultrasound transducer array 50 of the ultrasound observation part 36 of the distal end part 40 taken along a center line of an arc structure.

Figure 3:
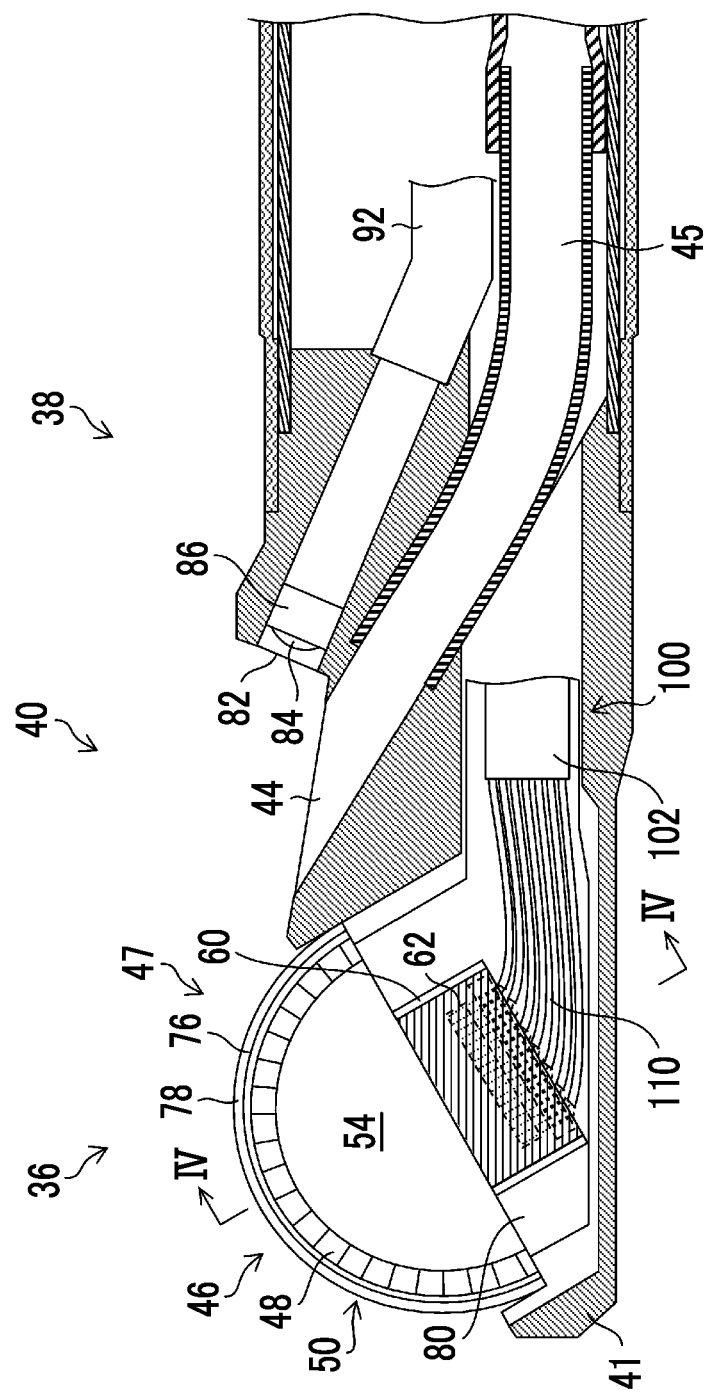
FIG. 3 is a cross-sectional view taken along the line of FIG. 2.

As shown in FIGS. 2 and 3, in the distal end part 40, the ultrasound observation part 36 that acquires an ultrasound image is mounted on the distal end side, and the endoscope observation part 38 that acquires an endoscope image is mounted on the proximal end side. In the distal end part 40, a treatment tool lead-out port 44 is provided between the ultrasound observation part 36 and the endoscope observation part 38.

The endoscope observation part 38 is configured with an observation window 82, an objective lens 84, a solid-state imaging element 86, illumination windows 88, a cleaning nozzle 90, a wiring cable 92, and the like.

The treatment tool lead-out port 44 is connected to a treatment tool channel 45 that is inserted into the insertion part 22. A treatment tool (not shown) inserted from the treatment tool insertion port 30 of FIG. 1 is let out from the treatment tool lead-out port 44 into the body cavity through the treatment tool channel 45.

Figure 4:
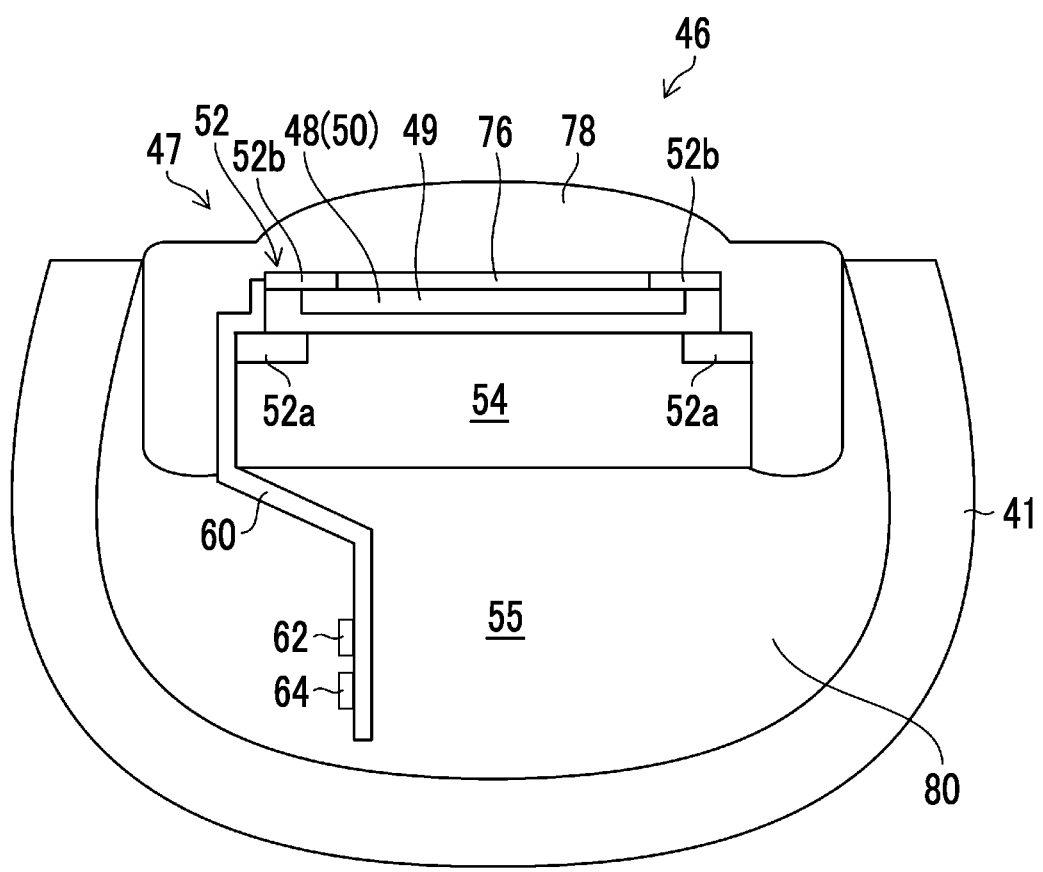
FIG. 4 is a cross-sectional view taken along the line IV-IV shown in FIG. 3.

As shown in FIGS. 2 to 4, the ultrasound observation part 36 comprises the ultrasound transducer unit 46, an exterior member 41 that holds the ultrasound transducer unit 46, and a cable 100 that is electrically connected to the ultrasound transducer unit 46 through a substrate 60. The exterior member 41 is made of a rigid member, such as rigid resin, and configures a part of the distal end part 40.

The ultrasound transducer unit 46 has the ultrasound transducer array 50 that consists of a plurality of ultrasound transducers 48, an electrode 52 that is provided on an end portion side of the ultrasound transducer array 50 in a width direction (a direction perpendicular to the longitudinal axis direction of the insertion part 22), a backing material layer 54 that supports each ultrasound transducer 48 from a lower surface side, the substrate 60 that is disposed along a side surface of the backing material layer 54 in the width direction and is connected to the electrode 52, and a filler layer 80 with which an internal space 55 between the exterior member 41 and the backing material layer 54 is filled.

As long as the substrate 60 can electrically connect a plurality of ultrasound transducers 48 and the cable 100, in particular, the structure thereof is not limited.

It is preferable that the substrate 60 is configured with, for example, a wiring substrate, such as a flexible substrate (flexible print substrate (also referred to as a flexible printed circuit (FPC)) having flexibility, a printed wiring circuit substrate (also referred to as a printed circuit board (PCB)) made of a rigid substrate having high rigidity with no flexibility, or a printed wiring substrate (also referred to as a printed wired board (PWB)).

The ultrasound transducer unit 46 has an acoustic matching layer 76 laminated on the ultrasound transducer array 50, and an acoustic lens 78 laminated on the acoustic matching layer 76. That is, the ultrasound transducer unit 46 is configured as a laminate 47 having the acoustic lens 78, the acoustic matching layer 76, the ultrasound transducer array 50, and the backing material layer 54.

The ultrasound transducer array 50 is configured with a plurality of rectangular parallelepiped ultrasound transducers 48 arranged in a convex arc shape outward. The ultrasound transducer array 50 is an array of 48 to 192 channels consisting of 48 to 192 ultrasound transducers 48, for example. Each of the ultrasound transducer 48 has a piezoelectric body 49.

The ultrasound transducer array 50 has the electrode 52. The electrode 52 has an individual electrode 52a individually and independently provided for each ultrasound transducer 48, and a transducer ground 52b that is a common electrode common to all the ultrasound transducers 48. In FIG. 4, a plurality of individual electrodes 52a are disposed on lower surfaces of end portions of a plurality of ultrasound transducers 48, and the transducer ground 52b is disposed on upper surfaces of the end portions of the ultrasound transducers 48.

The substrate 60 has 48 to 192 wirings (not shown) that are electrically connected to the individual electrodes 52a of the 48 to 192 ultrasound transducers 48, respectively, and a plurality of electrode pads 62 that are connected to the ultrasound transducers 48 through the wirings, respectively.

The ultrasound transducer array 50 has a configuration in which a plurality of ultrasound transducers 48 are arranged at a predetermined pitch in a one-dimensional array as an example. The ultrasound transducers 48 configuring the ultrasound transducer array 50 are arranged at regular intervals in a convex bent shape along an axial direction of the distal end part 40 (the longitudinal axis direction of the insertion part 22) and are sequentially driven based on drive signals input from the ultrasound processor device 14 (see FIG. 1). With this, convex electronic scanning is performed with a range where the ultrasound transducers 48 shown in FIG. 2 are arranged, as a scanning range.

The acoustic matching layer 76 is a layer that is provided for taking acoustic impedance matching between the subject and the ultrasound transducers 48.

The acoustic lens 78 is a lens that is provided for converging the ultrasonic waves emitted from the ultrasound transducer array 50 toward the observation target part. The acoustic lens 78 is formed of, for example, silicon-based resin (millable type silicon rubber, liquid silicon rubber, or the lie), butadiene-based resin, or polyurethane-based resin. In the acoustic lens 78, powder, such as titanium oxide, alumina, or silica, is mixed as necessary. With this, the acoustic lens 78 can take acoustic impedance matching between the subject and the ultrasound transducers 48 in the acoustic matching layer 76, and can increase the transmittance of the ultrasonic waves.

As shown in FIGS. 3 and 4, the backing material layer 54 is disposed on an inside with respect to the arrangement surface of a plurality of ultrasound transducers 48, that is, a rear surface (lower surface) of the ultrasound transducer array 50. The backing material layer 54 is made of a layer of a member made of a backing material. The backing material layer 54 has a role of mechanically and flexibly supporting the ultrasound transducer array 50 and attenuating ultrasonic waves propagated to the backing material layer 54 side among ultrasound signals emitted from a plurality of ultrasound transducers 48 or reflected propagated from the observation target. For this reason, the backing material is made of a material having rigidity, such as hard rubber, and an ultrasonic wave attenuation material (ferrite, ceramics, or the like) is added as needed.

The filler layer 80 is a layer with which the internal space 55 between the exterior member 41 and the backing material layer 54 is filled, and has a role of fixing the substrate 60, the non-coaxial cables 110, and various wiring portions. It is preferable that the acoustic impedance of the filler layer 80 matches the acoustic impedance of the backing material layer 54 with given accuracy or higher such that the ultrasound signals propagated from the ultrasound transducer array 50 to the backing material layer 54 side are not reflected at a boundary surface between the filler layer 80 and the backing material layer 54. It is preferable that the filler layer 80 is made of a member having heat dissipation to increase efficiency in dissipating heat generated in a plurality of ultrasound transducers 48. In a case where the filler layer 80 has heat dissipation, heat is received from the backing material layer 54, the substrate 60, the non-coaxial cables 110, and the like, and thus, heat dissipation efficiency can be improved.

With the ultrasound transducer unit 46 configured as described above, in a case where each ultrasound transducer 48 of the ultrasound transducer array 50 is driven, and a voltage is applied to the electrode 52 of the ultrasound transducer 48, the piezoelectric body 49 vibrates to sequentially generate ultrasonic waves, and the irradiation of the ultrasonic waves is performed toward the observation target part of the subject. Then, as a plurality of ultrasound transducers 48 are sequentially driven by an electronic switch, such as a multiplexer, scanning with ultrasonic waves is performed in a scanning range along a curved surface on which the ultrasound transducer array 50 is disposed, for example, a range of about several tens mm from the center of curvature of the curved surface.

In a case where the echo signal reflected from the observation target part is received, the piezoelectric body 49 vibrates to generate a voltage and outputs the voltage as an electric signal corresponding to the received ultrasound echo to the ultrasound processor device 14. Then, the electric signal is subjected to various kinds of signal processing in the ultrasound processor device 14 and is displayed as an ultrasound image on the monitor 20.

In the embodiment, the substrate 60 shown in FIG. 4 has, at one end, a plurality of electrode pads 62 that are electrically connected to a plurality of individual electrodes 52a, and a ground electrode pad 64 that is electrically connected to the transducer ground 52b. In FIG. 4, the cable 100 is omitted.

Electrical bonding of the substrate 60 and the individual electrodes 52a can be established by, for example, a resin material having conductivity. Examples of the resin material include an anisotropic conductive film (ACF) or an anisotropic conductive paste (ACP) obtained by mixing thermosetting resin with fine conductive particles and forming the mixture into a film.

As another resin material, for example, a resin material in which a conductive filler, such as metallic particles, is dispersed into binder resin, such as epoxy or urethane, and the filler forms a conductive path after adhesion may be used. Examples of this resin material include a conductive paste, such as a silver paste.

As shown in FIG. 3, the cable 100 comprises a plurality of non-coaxial cables 110, and an outer coat 102 with which a plurality of non-coaxial cables 110 are coated. Signal wires included in the non-coaxial cable 110 are electrically bonded to the electrode pads 62 of the substrate 60.

Next, a connection structure of the substrate 60 and the cable 100 will be described referring to the drawings.

Figure 5:
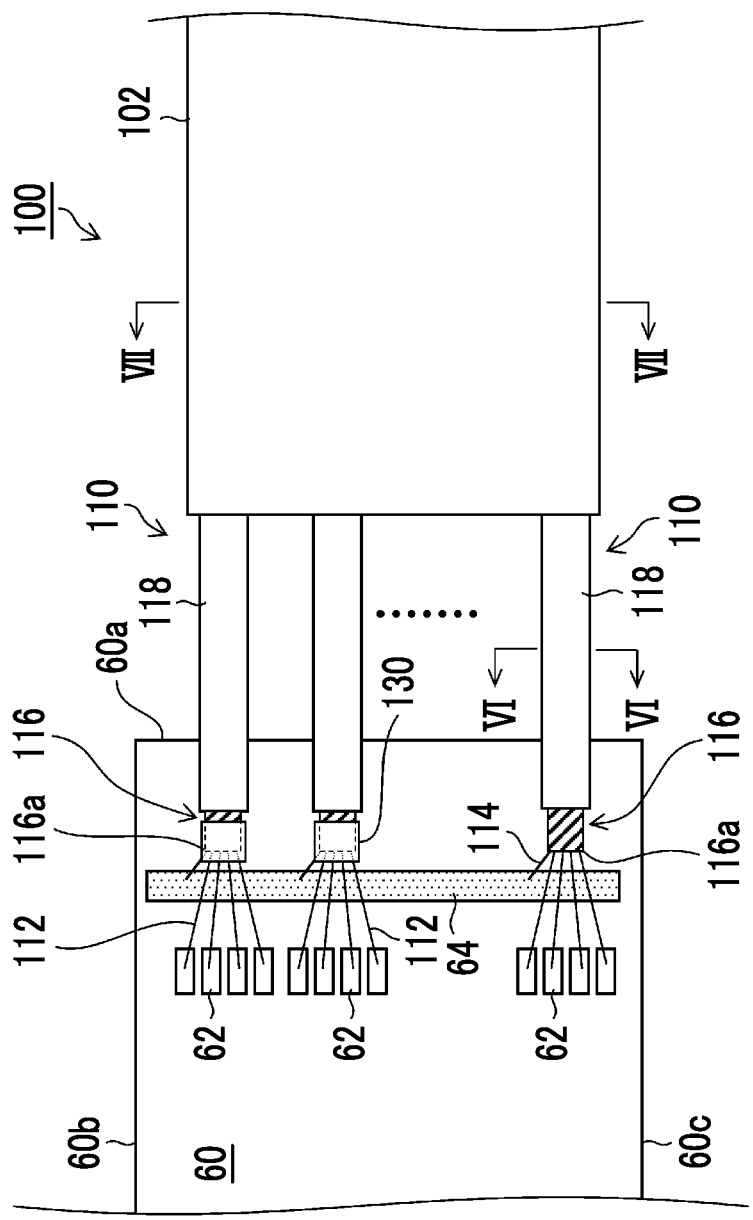
FIG. 5 is a diagram showing a connection structure of a substrate and non-coaxial cables.
Figure 6:
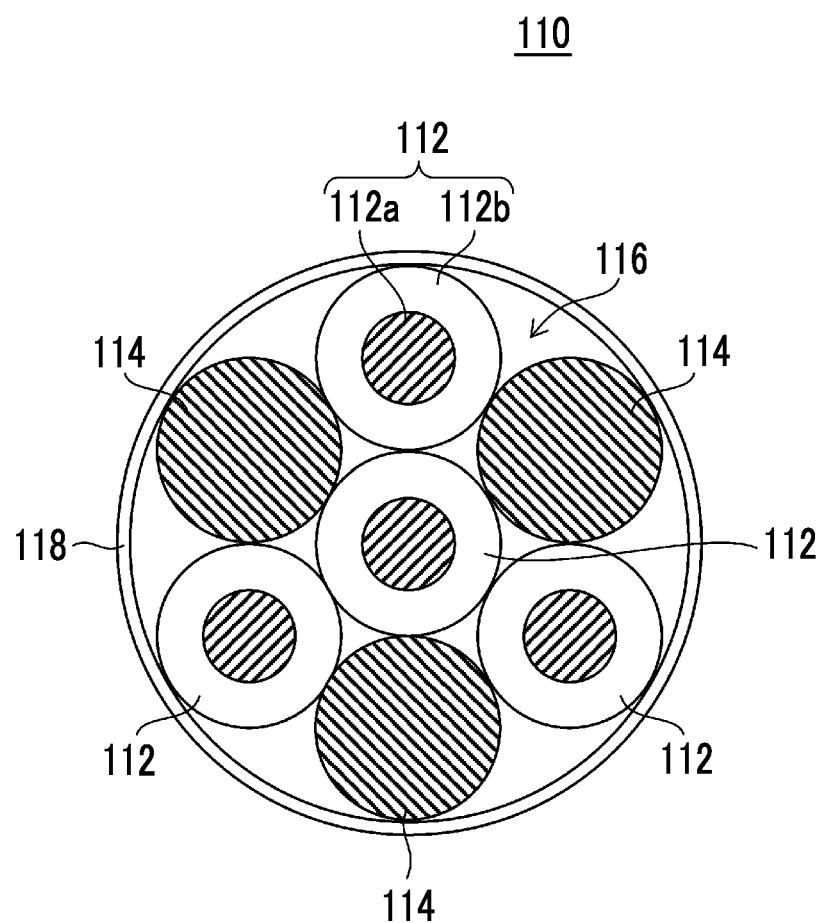
FIG. 6 is a cross-sectional view of a non-coaxial cable taken along the line VI-VI of FIG. 5.
Figure 7:
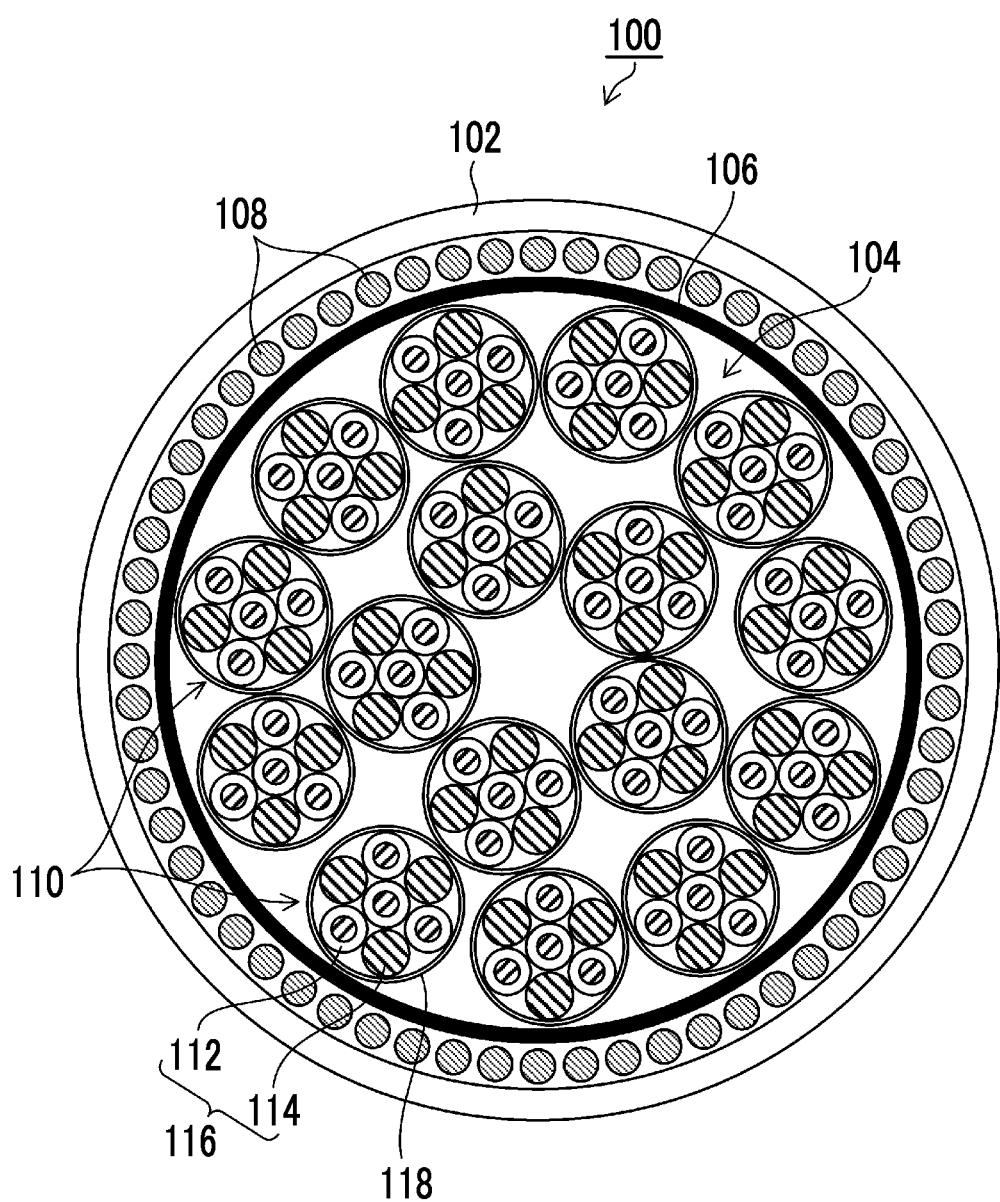
FIG. 7 is a cross-sectional view of a cable taken along the line VII-VII of FIG. 5.

FIG. 5 is an enlarged view of a portion including the substrate 60 and the cable 100. FIG. 6 is a cross-sectional view taken along the line VI-VI. FIG. 7 is a cross-sectional view taken along the line VII-VII.

As shown in FIG. 5, the substrate 60 has a plurality of electrode pads 62 disposed along a side 60a on a proximal end side, and the ground electrode pad 64 disposed between a plurality of electrode pads 62 and the side 60a. The ground electrode pad 64 is disposed in parallel to the side 60a.

The cable 100 is disposed at a position facing the side 60a of the substrate 60. The cable 100 comprises a plurality of non-coaxial cables 110, and the outer coat 102 that covers a plurality of non-coaxial cables 110. The electrode pads 62 and signal wires 112 of the non-coaxial cables 110 are electrically bonded. The non-coaxial cables 110 are disposed in parallel with a side 60b and a side 60c perpendicular to the side 60a. Note that a positional relationship between the substrate 60 and the non-coaxial cables 110 is not particularly limited.

Next, the structure of the non-coaxial cables 110 will be described. As shown in FIG. 6, the non-coaxial cable 110 has a plurality of signal wires 112 and a plurality of ground wires 114. Each signal wire 112 is made of, for example, a conductor 112a, and an insulating layer 112b with which the periphery of the conductor 112a is coated. The conductor 112a is made of, for example, an element wire, such as copper or copper alloy. The element wire is subjected to, for example, plating processing, such as tin plating or silver plating. The conductor 112a has a diameter of 0.03 mm to 0.04 mm.

The insulating layer 112b can be made of, for example, a resin material, such as fluorinated-ethylene-propylene (FEP) or perfluoroalkoxy (PFA). The insulating layer 112b has a thickness of 0.015 mm to 0.025 mm.

Each ground wire 114 is made of a conductor having the same diameter as the signal wire 112. The ground wire 114 is made of an element wire, such as copper or copper alloy, or a stranded wire obtained by stranding a plurality of element wires, such as copper or copper alloy.

A first cable bundle 116 is configured by stranding a plurality of signal wires 112 and a plurality of ground wires 114.

Each non-coaxial cable 110 comprises a first shield layer 118 with which the periphery of the first cable bundle 116 is coated. The first shield layer 118 can be made of an insulating film obtained by laminating metallic foils through an adhesive. The insulating film is made of a polyethylene terephthalate (PET) film. The metallic foil is made of an aluminum foil or a copper foil.

The non-coaxial cable 110 is shielded by the first shield layer 118 with a plurality of signal wires 112 as one set. The signal wires 112 are handled in a unit of the non-coaxial cable 110.

As shown in FIG. 6, in the non-coaxial cable 110 of the embodiment, the first cable bundle 116 is configured by stranding seven wires in total of four signal wires 112 and three ground wires. One signal wire 112 of the four signal wires 112 is disposed at the center. The remaining three signal wires 112 and the three ground wires 114 are disposed adjacently in the periphery of the signal wire 112 at the center. Note that the number of signal wires 112, the number of ground wires 114, and the disposition of the wires in the first cable bundle 116 are not limited to the structure of FIG. 6.

Next, the structure of the cable 100 will be described. As shown in FIG. 7, the cable 100 comprises a plurality of non-coaxial cables 110. A second cable bundle 104 is configured with a plurality of non-coaxial cables 110.

The second cable bundle 104 is coated with the outer coat 102. The outer coat 102 can be made of a fluorine-based resin material, such as extruded and coated PFA, FEP, an ethylene/ethylene tetrafluoride copolymer (ETFE), or polyvinyl chloride (PVC). The outer coat 102 can be made of a wound resin tape (PET tape). The coating of the second cable bundle 104 with the outer coat 102 includes a case where the outside of the second cable bundle 104 is coated directly and a case where the outside of the second cable bundle 104 is coated indirectly. Indirect coating includes disposing another layer between the outer coat 102 and the second cable bundle 104.

The cable 100 of the embodiment comprises, in order from the inside, a resin layer 106 and a second shield layer 108 between the outer coat 102 and the second cable bundle 104. The second cable bundle 104 is coated with the resin layer 106. The resin layer 106 can be made of, for example, the fluorine-based resin material or the resin tape described above.

The second shield layer 108 may be configured by, for example, braiding a plurality of element wires. The element wire is made of a copper wire, a copper alloy wire, or the like subjected to plating processing (tin plating or silver plating).

The cable 100 may not comprise both the resin layer 106 and the second shield layer 108 other than the above-described configuration or may comprise only one of the resin layer 106 or the second shield layer 108.

The cable 100 of the embodiment includes 16 non-coaxial cables 110, and includes 64 signal wires 112. The number of non-coaxial cables 110 and the number of signal wires 112 are not limited to the numerical values.

As described above, the non-coaxial cable 110 included in the cable 100 does not comprise a shield layer and an outer coat for each signal wire 112, unlike the coaxial cable in the related art. In particular, in a case where the cable 100 is configured with a plurality of non-coaxial cables 110, the cable 100 can be reduced in diameter compared to the coaxial cable in the related art. In a case where the outer diameter is the same as the outer diameter of the coaxial cable, the cable 100 can comprise a greater number of signal wires 112 than the coaxial cable in the related art.

Next, a connection structure of the substrate 60 and the non-coaxial cables 110 will be described in detail. As shown in FIG. 5, on the proximal end side of the substrate 60, the resin layer 106 (not shown), the second shield layer 108 (not shown), and the outer coat 102 of the cable 100 are removed, and a plurality of non-coaxial cables 110 are exposed. On the proximal end side of the substrate 60, the first shield layer 118 of each non-coaxial cable 110 is removed, and the first cable bundle 116 is exposed.

The first shield layer 118 is positioned on the substrate 60, and the substrate 60 and the first shield layer 118 overlap at least partially as viewed from a direction perpendicular to a principal surface of the substrate 60 (hereinafter, referred to as plan view). The first cable bundle 116 is exposed only on the substrate 60, and the substrate 60 and the first cable bundle 116 overlap only on the substrate 60. A part of the first cable bundle 116 may protrude from the substrate 60.

The substrate 60 and the first cable bundle 116 are fixed by a fixing part 130, and the relative positions of the substrate 60 and each first cable bundle 116 are fixed. The position and the size of the fixing part 130 are not limited as long as the relative positions of the substrate 60 and each first cable bundle 116 are fixed. The first cable bundle 116 configured with a stranded wire of a plurality of signal wires 112 and a plurality of ground wires 114 is unstranded into the respective signal wires 112 at a distal end 116a. Each unstranded signal wire 112 is electrically bonded to the electrode pad 62 disposed on the substrate 60. The distal end 116a is a start position where each signal wire 112 is unstranded. In some first cable bundles 116, the fixing part 130 is omitted for ease of understanding.

In the embodiment, the substrate 60 and the first cable bundle 116 are fixed by the fixing part 130. Accordingly, when stress is applied to the cable 100 or the non-coaxial cable 110, stress is prevented from being transmitted to a bonded portion of the electrode pad 62 and the signal wire 112, and disconnection of the signal wire 112 can be prevented.

The fixing part 130 is not particularly limited as long as the relative positional relationship between the substrate 60 and the first cable bundle 116 can be fixed, and for example, any one of an adhesive, solder, or a clamp member, or a combination thereof can be applied. The fixing part 130 can individually fix the substrate 60 and the first cable bundle 116 or can fix the substrate 60 and a plurality of first cable bundles 116 in a lump.

The ground wires 114 of each first cable bundle 116 are electrically bonded to the ground electrode pad 64 of the substrate 60. At least one ground wire 114 included in each first cable bundle 116 is electrically bonded to the ground electrode pad 64. A plurality of ground wires 114 are in contact with each other in the first cable bundle 116. Accordingly, at least one ground wire 114 of each first cable bundle 116 is electrically bonded to the ground electrode pad 64, where the ground potentials of a plurality of first cable bundles 116 can be at the same potential. A region occupied by the wires can be reduced by reducing the number of ground wires 114 that are electrically bonded to the ground electrode pad 64. As a result, it is possible to achieve reduction in diameter of the distal end part 40.

In the connection structure shown in FIG. 5, the electrode pads 62 corresponding to each non-coaxial cable 110 are collectively disposed. That is, four electrode pads 62 that are electrically bonded to the four signal wires 112 are collectively disposed on the substrate 60. It is preferable that the electrode pads 62 corresponding to the non-coaxial cable 110 are the electrode pads 62 that are disposed substantially in an extension direction of the non-coaxial cable 110. It is preferable that the signal wires 112 of each non-coaxial cable 110 are not electrically bonded to the electrode pads 62 of an adjacent non-coaxial cable 110. It is possible to prevent stress from being applied to the signal wires 112.

Figure 8:
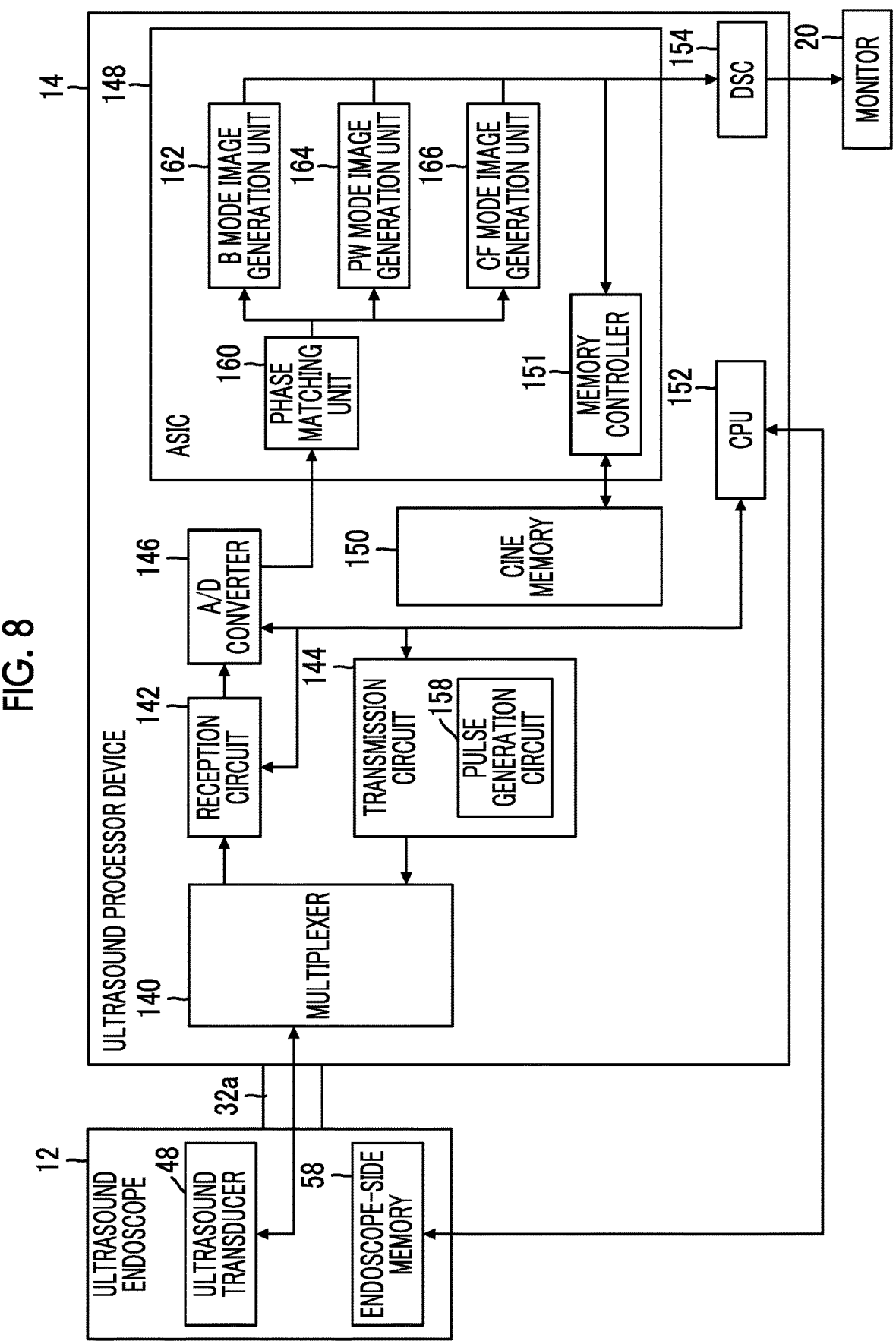
FIG. 8 is a block diagram showing the configuration of an ultrasound processor device shown in FIG. 1.

FIG. 8 is a block diagram showing the configuration of an ultrasound processor device. As shown in FIG. 8, the ultrasound processor device 14 has a multiplexer 140, a reception circuit 142, a transmission circuit 144, an A/D converter 146, an application specific integrated circuit (ASIC) 148, a cine memory 150, a central processing unit (CPU) 152, and a digital scan converter (DSC) 154.

The reception circuit 142 and the transmission circuit 144 are electrically connected to the ultrasound transducer array 50 of the ultrasound endoscope 12. The multiplexer 140 selects a maximum of m drive target ultrasound transducers from among n ultrasound transducers 48 and opens the channels.

The transmission circuit 144 has a field programmable gate array (FPGA), a pulser (pulse generation circuit 158), a switch (SW), and the like, and is connected to the multiplexer 140 (MUX). An application-specific integrated circuit (ASIC), instead of the FPGA, may be used.

The transmission circuit 144 is a circuit that supplies a drive voltage for ultrasonic wave transmission to the drive target ultrasound transducers 48 selected by the multiplexer 140 in response to a control signal sent from the CPU 152 for transmission of ultrasonic waves from the ultrasound transducer unit 46. The drive voltage is a pulsed voltage signal (transmission signal) and is applied to the electrodes of the drive target ultrasound transducers 48 through the universal cord 26 and the cable 100. In detail, the drive voltage is applied to the electrode through the signal wires 112 of the non-coaxial cable 110 of the cable 100.

The transmission circuit 144 has a pulse generation circuit 158 that generates a transmission signal based on a control signal. Under the control of the CPU 152, the transmission circuit 144 generates a transmission signal for driving a plurality of ultrasound transducers 48 to generate ultrasonic waves using the pulse generation circuit 158 and supplies the transmission signal to a plurality of ultrasound transducers 48.

In a case of performing ultrasonography, the transmission circuit 144 generates the transmission signal of the drive voltage for performing ultrasonography using the pulse generation circuit 158 under the control of the CPU 152.

The reception circuit 142 is a circuit that receives electric signals output from the drive target ultrasound transducers 48, which receive the ultrasonic waves (echoes), that is, reception signals. The reception circuit 142 comprises an amplifier that amplifies the reception signal, and as needed, an attenuator that attenuates the reception signals. A gain value of the amplifier that amplifies the reception signals is set in response to a control signal of the CPU 152. An attenuation value of the attenuator that attenuates the reception signal is set in response to a control signal of the CPU 152.

The reception circuit 142 amplifies the reception signals received from the ultrasound transducers 48 in response to a control signal sent from the CPU 152 and delivers the signals after amplification to the A/D converter 146. The A/D converter 146 is connected to the reception circuit 142, converts the reception signals received from the reception circuit 142 from analog signals to digital signals, and outputs the digital signals after conversion to the ASIC 148.

The ASIC 148 is connected to the A/D converter 146. As shown in FIG. 8, the ASIC 148 configures a phase matching unit 160, a B mode image generation unit 162, a PW mode image generation unit 164, a CF mode image generation unit 166, and a memory controller 151.

In the embodiment, although the above-described functions (specifically, the phase matching unit 160, the B mode image generation unit 162, the PW mode image generation unit 164, the CF mode image generation unit 166, and the memory controller 151) are realized by a hardware circuit, such as the ASIC 148, the invention is not limited thereto. The above-described functions may be realized by the cooperation of a central processing unit (CPU) and software (computer program) for executing various kinds of data processing.

The phase matching unit 160 executes processing of giving a delay time to the reception signals (reception data) digitized by the A/D converter 146 and performing phasing addition (performing addition after matching the phases of the reception data). With the phasing addition processing, sound ray signals in which the focus of the ultrasound echo is narrowed are generated.

The B mode image generation unit 162, the PW mode image generation unit 164, and the CF mode image generation unit 166 generate an ultrasound image based on the electric signals (strictly, sound ray signals generated by phasing addition on the reception data) output from the drive target ultrasound transducers among a plurality of ultrasound transducers 48 when the ultrasound transducer unit 46 receives the ultrasonic waves.

A brightness (B) mode is a mode in which amplitude of an ultrasound echo is converted into brightness and a tomographic image is displayed. A pulse wave (PW) mode is a mode in which a speed (for example, a rate of a blood flow) of an ultrasound echo source detected based on transmission and reception of a pulse wave is displayed. A color flow (CF) mode is a mode in which an average blood flow rate, flow fluctuation, intensity of a flow signal, flow power, and the like are mapped to various colors and displayed on a B mode image in a superimposed manner.

The B mode image generation unit 162 is an image generation unit that generates a B mode image as a tomographic image of the inside (the inside of the body cavity) of the patient. The B mode image generation unit 162 performs correction of attenuation due to a propagation distance on each of the sequentially generated sound ray signals according to a depth of a reflection position of the ultrasonic wave through sensitivity time gain control (STC). Furthermore, the B mode image generation unit 162 executes envelope detection processing and logarithm (Log) compression processing on the sound ray signal after correction to generate a B mode image (image signal).

The PW mode image generation unit 164 is an image generation unit that generates an image indicating a rate of a blood flow in a predetermined direction. The PW mode image generation unit 164 extracts a frequency component by performing fast Fourier transform on a plurality of sound ray signals in the same direction among the sound ray signals sequentially generated by the phase matching unit 160. Thereafter, the PW mode image generation unit 164 calculates the rate of the blood flow from the extracted frequency component and generates a PW mode image (image signal) indicating the calculated rate of the blood flow.

The CF mode image generation unit 166 is an image generation unit that generates an image indicating information regarding a blood flow in a predetermined direction. The CF mode image generation unit 166 generates an image signal indicating information regarding the blood flow by obtaining autocorrelation of a plurality of sound ray signals in the same direction among the sound ray signals sequentially generated by the phase matching unit 160. Thereafter, the CF mode image generation unit 166 generates a CF mode image (image signal) as a color image, in which information relating to the blood flow is superimposed on the B mode image signal generated by the B mode image generation unit 162, based on the above-described image signal.

The above-described ultrasound image generation modes are merely an example, and modes other than the above-described three kinds of modes, for example, an amplitude (A) mode, a motion (M) mode, and a contrast radiography mode may be further include or a mode in which a Doppler image is obtained may be included.

The memory controller 151 stores the image signal generated by the B mode image generation unit 162, the PW mode image generation unit 164, or the CF mode image generation unit 166 in the cine memory 150.

The DSC 154 is connected to the ASIC 148, converts (raster conversion) the signal of the image generated by the B mode image generation unit 162, the PW mode image generation unit 164, or the CF mode image generation unit 166 into an image signal compliant with a normal television signal scanning system, executes various kinds of necessary image processing, such as gradation processing, on the image signal, and then, outputs the image signal to the monitor 20.

The cine memory 150 has a capacity for accumulating an image signal for one frame or image signals for several frames. An image signal generated by the ASIC 148 is output to the DSC 154 and is stored in the cine memory 150 by the memory controller 151. In a freeze mode, the memory controller 151 reads out the image signal stored in the cine memory 150 and outputs the image signal to the DSC 154. With this, an ultrasound image (static image) based on the image signal read from the cine memory 150 is displayed on the monitor 20.

The CPU 152 functions as a controller (control circuit) that controls each unit of the ultrasound processor device 14, is connected to the reception circuit 142, the transmission circuit 144, the A/D converter 146, and the ASIC 148, and controls such circuits.

In a case where the ultrasound endoscope 12 is connected to the ultrasound processor device 14 through the ultrasound connector 32a, the CPU 152 automatically recognizes the ultrasound endoscope 12 by a method, such as Plug and Play (PnP).

Incidentally, the cable 100 used in the embodiment includes a plurality of non-coaxial cables 110. As shown in FIG. 6, the non-coaxial cable 110 is not provided with a shield layer for each signal wire 112, unlike a coaxial cable.

As a result, in a case of the non-coaxial cable 110, the signal wires 112 may be affected by the magnitude of static capacitance depending on the disposition in the first cable bundle 116. For example, the static capacitance of the signal wire 112 disposed at the center of the non-coaxial cable 110 is smaller than the static capacitance of a plurality of signal wires 112 disposed in the periphery.

The static capacitance of the signal wire 112 is affected by transmission and reception sensitivity of the ultrasound transducer 48 to which the signal wire 112 is electrically connected. A difference (variation) in static capacitance between the signal wire 112 results in a difference in sensitivity, and as a result, there is a concern that image quality deterioration (for example, image quality unevenness) of an ultrasound image occurs. Here, the transmission and reception sensitivity is defined as a ratio of the amplitude of the electric signal output from the ultrasound transducer 48 with reception of the ultrasonic wave to the amplitude of the ultrasonic wave transmitted from the ultrasound transducer 48.

Figure 9A:
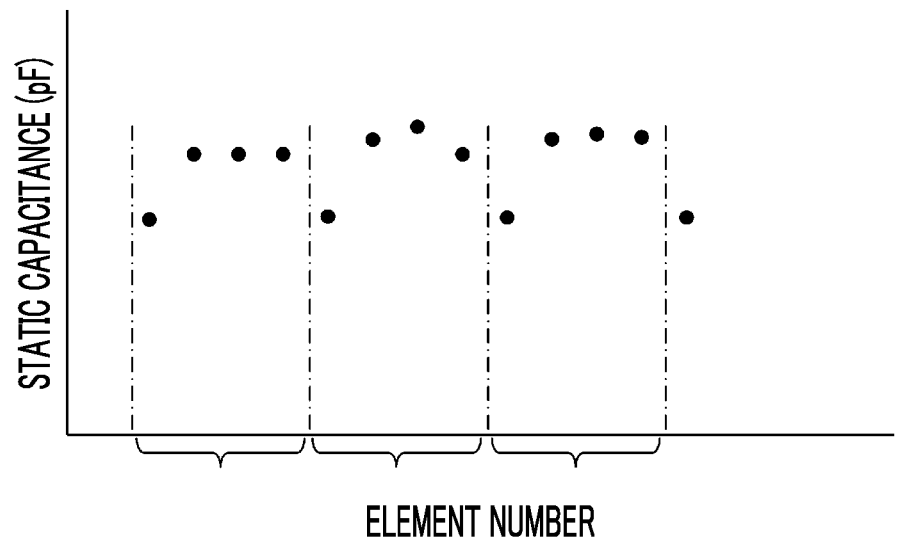
FIGS. 9A and 9B are graphs showing a relationship between an ultrasound transducer and static capacitance, and a relationship between the ultrasound transducer and transmission and reception sensitivity, respectively.

FIG. 9A is a graph showing a relationship between an ultrasound transducer and static capacitance. The vertical axis indicates static capacitance (pF), and the horizontal axis indicates an element number of an ultrasound transducer. The graph shows the static capacitance of the signal wire connected to each ultrasound transducer. The element number is a number allocated to identify each ultrasound transducer. As shown in the graph of FIG. 9A, the static capacitance of each signal wire is not constant, and there is a difference in static capacitance between the signal wires periodically in a unit of the first cable bundle. Brackets in the drawing indicate the signal wires included in each first cable bundle (the same applies to FIGS. 10 and 11).

Figure 9B:
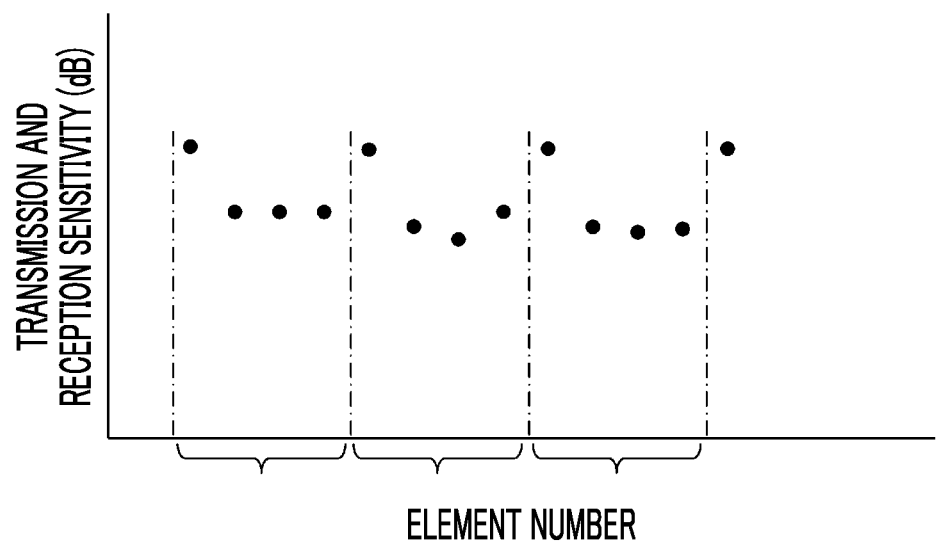

FIG. 9B is a graph showing a relationship between an ultrasound transducer and transmission and reception sensitivity. The vertical axis indicates transmission and reception sensitivity (dB), and the horizontal axis indicates an element number of an ultrasound transducer. As shown in the graph of FIG. 9B, the transmission and reception sensitivity of each ultrasound transducer is not constant due to the static capacitance of the signal wire. The magnitude of the transmission and reception sensitivity is different periodically between a plurality of ultrasound transducers for each first cable bundle. As shown in FIG. 9B, compared to the static capacitance of FIG. 9A, in a case where the static capacitance of the signal wire decreases, the transmission and reception sensitivity increases, and in a case where the static capacitance of the signal wire increases, the transmission and reception sensitivity decreases. In a case where there is a difference in transmission and reception sensitivity between a plurality of ultrasound transducers, there is a concern that image quality deterioration of an ultrasound image occurs.

In the ultrasonography system 10 of the embodiment, to decrease the difference in transmission and reception sensitivity between a plurality of ultrasound transducers 48, the transmission and reception sensitivity of the ultrasound transducers 48 is corrected. The correction of the transmission and reception sensitivity will be described referring to the block diagram of FIG. 8.

To correct the transmission and reception sensitivity, static capacitance data indicating the static capacitance of the signal wire 112 (not shown) included in the first cable bundle 116 is stored in, for example, an endoscope-side memory 58 as an example of a memory where the static capacitance data is associated with the element number of the ultrasound transducer 48. The static capacitance data is acquired, for example, measuring the static capacitance of each signal wire 112. The static capacitance of the signal wire 112 can be measured, for example, before shipment after the ultrasound endoscope 12 is assembled.

The relationship between the static capacitance of each signal wire 112 of the first cable bundle 116 and the ultrasound transducer 48 is different for each ultrasound endoscope 12, and thus, the static capacitance data is stored in the endoscope-side memory 58 provided in the ultrasound endoscope 12. Note that the memory that stores the static capacitance data is not limited to the endoscope-side memory 58, and may be a memory provided in the ultrasound processor device 14. First, the static capacitance data of the ultrasound endoscope 12 is stored in the memory provided in the ultrasound processor device 14. In a case where the ultrasound processor device 14 recognizes the connection of the ultrasound endoscope 12, the static capacitance data corresponding to the ultrasound endoscope 12 used by the ultrasound processor device 14 may be read.

in a case where the ultrasound endoscope 12 is connected to the ultrasound processor device 14 through the ultrasound connector 32a, the CPU 152 automatically recognizes the ultrasound endoscope 12. The CPU 152 can access the static capacitance data stored in the endoscope-side memory 58 of the ultrasound endoscope 12.

The CPU 152 as a processor periodically corrects the transmission and reception sensitivity of each ultrasound transducer 48 based on the static capacitance data stored in the endoscope-side memory 58, and decreases the difference in transmission and reception sensitivity of each ultrasound transducer 48 compared to before correction. The transmission and reception sensitivity is periodically corrected, and the difference of the transmission and reception sensitivity is decreased, whereby image quality deterioration of an ultrasound image is suppressed.

An example where the transmission and reception sensitivity of each ultrasound transducer 48 is periodically corrected based on the static capacitance data of the signal wire 112 has been described. In addition, it is preferable that transmission and reception sensitivity due to a difference in sensitivity of each ultrasound transducer 48 is corrected.

For example, the sensitivity of the ultrasound transducer 48 is stored in the endoscope-side memory 58 in addition to the static capacitance data of the signal wire 112. The CPU 152 corrects the transmission and reception sensitivity of each ultrasound transducer 48 based on the static capacitance data and the sensitivity data stored in the accessible endoscope-side memory 58, and decreases the difference in transmission and reception sensitivity of each ultrasound transducer 48 compared to before correction. The transmission and reception sensitivity is corrected based on the static capacitance data and the sensitivity data, and the difference in transmission and reception sensitivity is decreased, whereby image quality deterioration of an ultrasound image is suppressed.

The sensitivity of the ultrasound transducer 48 can be acquired by measuring the ultrasound transducer 48 or from characteristic data when the ultrasound transducer 48 is obtained.

Next, a preferred form for periodically correcting the transmission and reception sensitivity will be described. A first form is a case where the transmission circuit 144 is used. The CPU 152 drives the ultrasound transducer 48 connected to the signal wire 112 having high static capacitance with a transmission signal of a higher voltage than the ultrasound transducer 48 connected to the signal wire 112 having low static capacitance.

First, the CPU 152 specifies the ultrasound transducer 48 connected to the signal wire 112 having high static capacitance and the ultrasound transducer 48 connected to the signal wire 112 having low static capacitance based on the static capacitance data stored in the endoscope-side memory 58.

The pulse generation circuit 158 generates a transmission signal of a higher voltage than a transmission signal for driving the ultrasound transducer 48 connected to the signal wire 112 having low static capacitance under the control of the CPU 152 for the ultrasound transducer 48 connected to the signal wire 112 having high static capacitance. The transmission circuit 144 supplies, for example, a transmission signal of a rated voltage to the ultrasound transducer 48 connected to the signal wire 112 having low static capacitance, supplies a transmission signal of a higher voltage than the rated voltage to the ultrasound transducer 48 connected to the signal wire 112 having high static capacitance, and drives a plurality of ultrasound transducers 48. For example, in a case where the drive voltage of the transmission signal of the ultrasound transducer 48 is 60 V, the drive voltage of the transmission signal of the ultrasound transducer 48 connected to the signal wire 112 having high static capacitance is set to 63 V.

Figure 10:
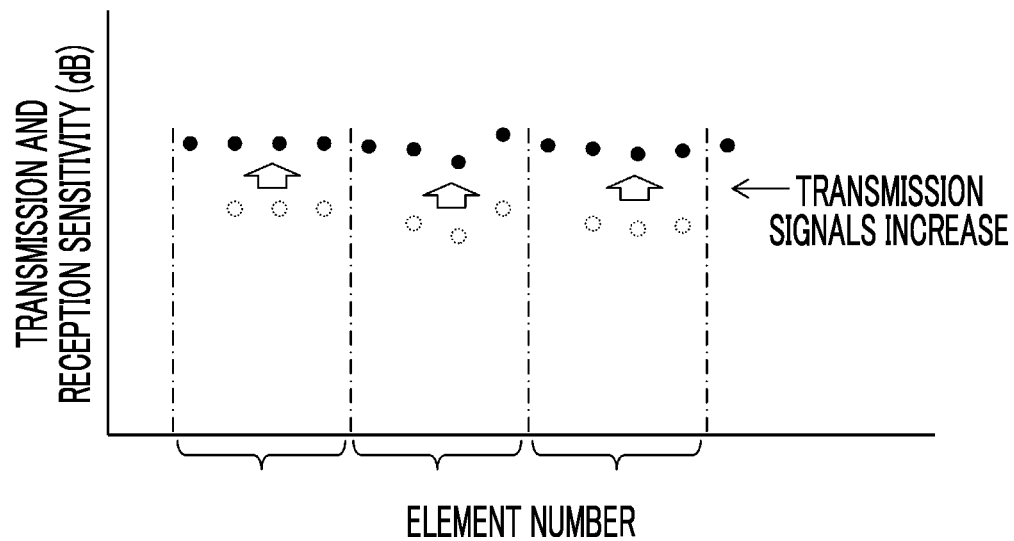
FIG. 10 is a graph showing a relationship between the ultrasound transducer and the transmission and reception sensitivity of a first form.

FIG. 10 is a graph showing a relationship between the ultrasound transducers and the transmission and reception sensitivity after correction. The transmission and reception sensitivity of the ultrasound transducer 48 can be increased by increasing the drive voltage of the transmission signal of the ultrasound transducer 48 connected to the signal wire 112 having high static capacitance (transmission signal increase). As a result, the difference in transmission and reception sensitivity between the ultrasound transducer 48 can be decreased compared to before correction.

Next, a preferred second form for periodically correcting the transmission and reception sensitivity will be described. The second form is a case where the reception circuit 142 is used. The CPU 152 applies a higher gain value to the reception signal to the ultrasound transducer 48 connected to the signal wire 112 having high static capacitance than the reception signal from the ultrasound transducer 48 connected to the signal wire 112 having low static capacitance.

First, the CPU 152 specifies the ultrasound transducer 48 connected to the signal wire 112 having high static capacitance and the ultrasound transducer 48 connected to the signal wire 112 having low static capacitance based on the static capacitance data stored in the endoscope-side memory 58.

The amplifier of the reception circuit 142 sets the gain value to the ultrasound transducer 48 connected to the signal wire 112 having high static capacitance higher than the gain value set to the ultrasound transducer 48 connected to the signal wire 112 having low static capacitance under the control of the CPU 152.

The reception circuit 142 applies a given gain value to the ultrasound transducer 48 connected to the signal wire 112 having low static capacitance, applies a gain value higher than the given gain value to the ultrasound transducer 48 connected to the signal wire 112 having high static capacitance, and amplifies the reception signals received from the ultrasound transducers 48.

Figure 11:
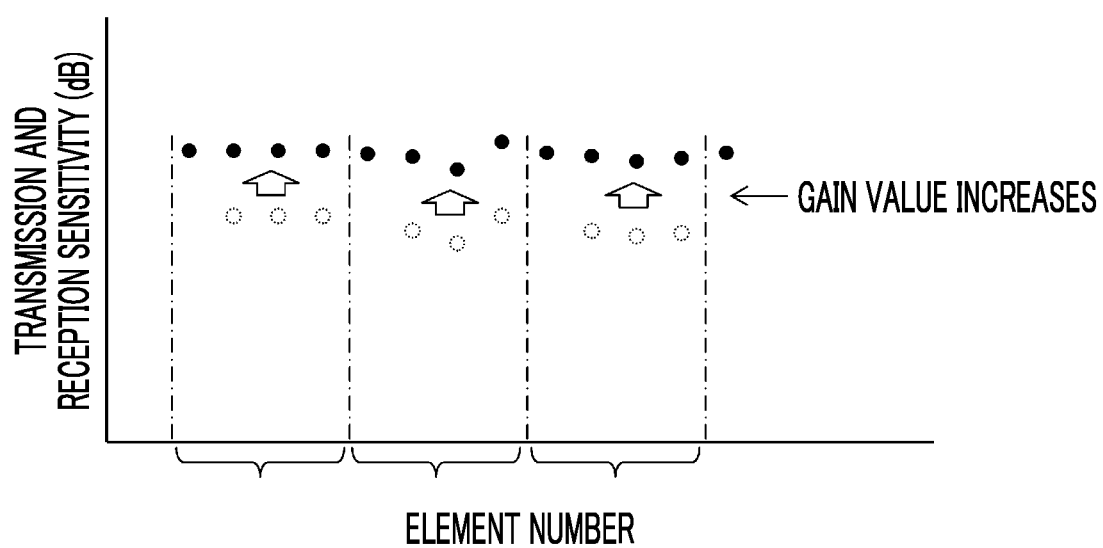
FIG. 11 is a graph showing a relationship between the ultrasound transducer and the transmission and reception sensitivity of a second form.

FIG. 11 is a graph showing a relationship between the ultrasound transducers and the transmission and reception sensitivity after correction. The transmission and reception sensitivity of the ultrasound transducer 48 can be increased by increasing the gain value of the ultrasound transducer 48 connected to the signal wire 112 having high static capacitance (gain value increases). As a result, the difference in transmission and reception sensitivity between the ultrasound transducer 48 can be decreased compared to before correction.

Next, a preferred third form for periodically correcting the transmission and reception sensitivity will be described. The third form is a case where the reception circuit 142 is used. The CPU 152 applies a higher attenuation value to the reception signal from the ultrasound transducer 48 connected to the signal wire 112 having low static capacitance than the reception signal from the ultrasound transducer 48 connected to the signal wire 112 having high static capacitance.

First, the CPU 152 specifies the ultrasound transducer 48 connected to the signal wire 112 having high static capacitance and the ultrasound transducer 48 connected to the signal wire 112 having low static capacitance based on the static capacitance data stored in the endoscope-side memory 58.

The attenuator of the reception circuit 142 sets the attenuation value to the ultrasound transducer 48 connected to the signal wire 112 having low static capacitance higher than the attenuation value set to the ultrasound transducer 48 connected to the signal wire 112 having high static capacitance under the control of the CPU 152.

The reception circuit 142 applies a given attenuation value to the ultrasound transducer 48 connected to the signal wire 112 having high static capacitance, applies an attenuation value greater than the given attenuation value to the ultrasound transducer 48 connected to the signal wire 112 having low static capacitance, and attenuates the reception signals received from the ultrasound transducers 48.

Figure 12:
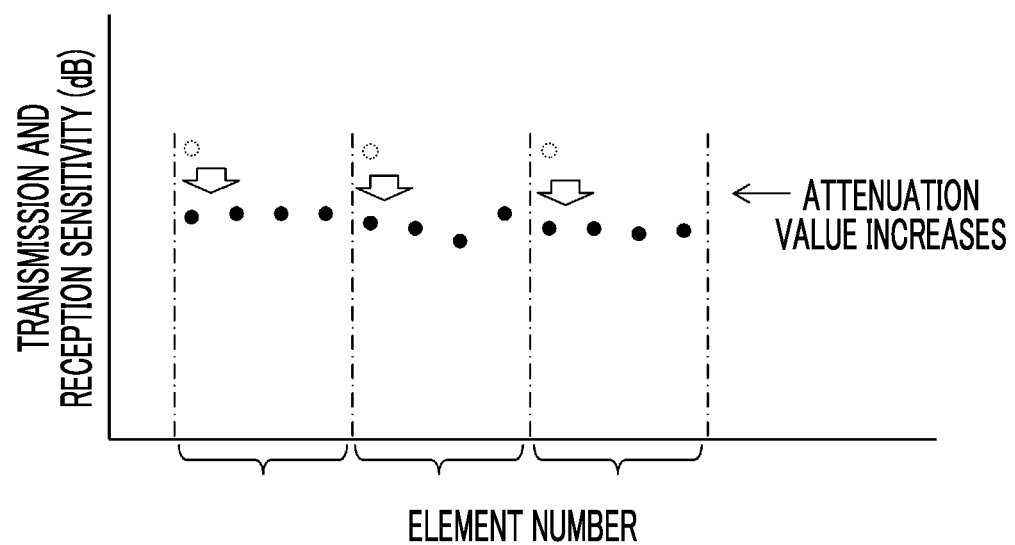
FIG. 12 is a graph showing a relationship between the ultrasound transducer and the transmission and reception sensitivity of a third form.

FIG. 12 is a graph showing a relationship between the ultrasound transducers and the transmission and reception sensitivity after correction. The transmission and reception sensitivity of the ultrasound transducer 48 can be decreased by increasing the attenuation value of the ultrasound transducer 48 connected to the signal wire 112 having low static capacitance (attenuation value increases). As a result, the difference in transmission and reception sensitivity between the ultrasound transducer 48 can be decreased compared to before correction.

In regard to the third form, the attenuation value may be decided at the time of shipment of the ultrasound endoscope 12. For example, the endoscope-side memory 58 stores the signal wire 112, the ultrasound transducer 48, and the attenuation value in association with the static capacitance of the signal wire 112. The attenuation value can be applied to the reception signal based on the stored ultrasound transducer 48 and attenuation value.

It is preferable that the difference in transmission and reception sensitivity between the ultrasound transducers 48 is equal to or less than 2 dB. In a case where this range is set, image quality deterioration of an ultrasound image can be prevented.

Figure 13A:
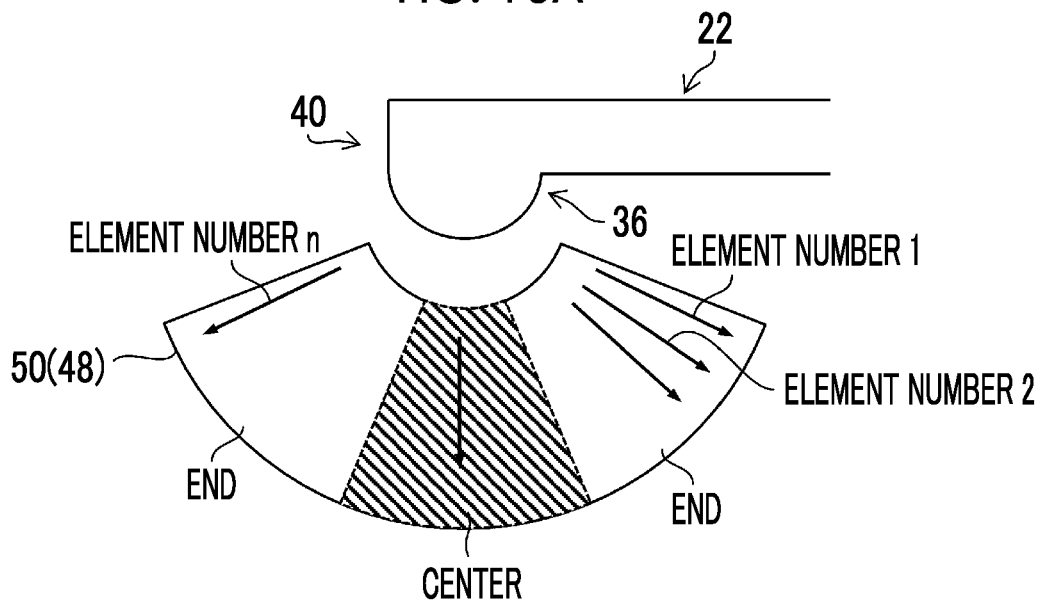
FIG. 13A is a conceptual diagram of scanning lines corresponding to ultrasound transducers of an ultrasound transducer array.
Figure 13B:
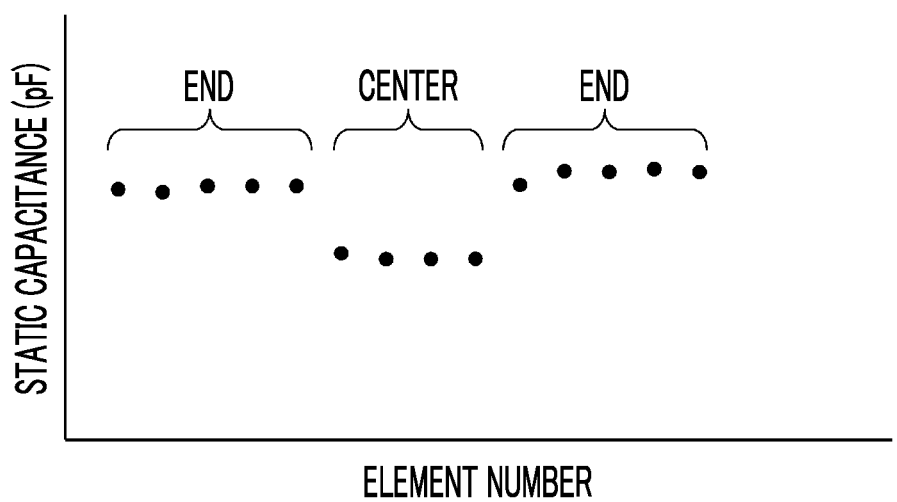
FIG. 13B is a graph showing a relationship between disposed ultrasound transducers and static capacitance.

Next, preferred disposition of the ultrasound transducers 48 in the ultrasound transducer array 50 will be described. FIG. 13A is a conceptual diagram of scanning lines corresponding to the ultrasound transducers of the ultrasound transducer array. FIG. 13B is a graph showing a relationship between the disposed ultrasound transducers and the static capacitance.

As shown in FIG. 13A, the ultrasound transducer array 50 is configured with a plurality of ultrasound transducers 48 of, for example, an element number 1 to an element number n. FIG. 13A shows scanning lines corresponding to the element numbers. In the ultrasound transducer array 50, the ultrasound transducer 48 connected to the signal wire 112 having low static capacitance is disposed on the center side. The ultrasound transducers 48 connected to the signal wires 112 having high static capacitance are disposed at ends positioned on both sides of the center.

As shown in the graph of FIG. 13B, the static capacitance of the ultrasound transducer 48 disposed on the center side is lower than the static capacitance of the ultrasound transducer 48 disposed at the end.

In a case where the ultrasound image is generated with the ultrasound endoscope 12, an ultrasound image generated by the ultrasound transducer 48 at the center of the ultrasound transducer array 50 is important. Accordingly, even though correction is not needed, the ultrasound transducer 48 having high transmission and reception sensitivity is disposed on the center side of the ultrasound transducer array 50, whereby an ultrasound image can be generated with higher accuracy than the ultrasound transducer 48 where correction is needed.

Although the invention has been described, the invention is not limited to the above-described example, and various improvements or modifications may be of course made without departing from the spirit and scope of the invention.

EXPLANATION OF REFERENCES

- 10: ultrasonography system
- 12: ultrasound endoscope
- 14: ultrasound processor device
- 16: endoscope processor device
- 18: light source device
- 20: monitor
- 21a: water supply tank
- 21b: suction pump
- 22: insertion part
- 24: operating part
- 26: universal cord
- 28a: air and water supply button
- 28b: suction button
- 29: angle knob
- 30: treatment tool insertion port
- 32a: connector
- 32b: connector
- 32c: connector
- 34a: air and water supply tube
- 34b: suction tube
- 36: ultrasound observation part
- 38: endoscope observation part
- 40: distal end part
- 41: exterior member
- 42: bending part
- 43: flexible part
- 44: treatment tool lead-out port
- 45: treatment tool channel
- 46: ultrasound transducer unit
- 47: laminate
- 48: ultrasound transducer
- 49: piezoelectric body
- 50: ultrasound transducer array
- 52: electrode
- 52a: individual electrode
- 52b: transducer ground
- 54: backing material layer
- 55: internal space
- 58: endoscope-side memory
- 60: substrate
- 60a: side
- 60b: side
- 60c: side
- 62: electrode pad
- 64: ground electrode pad
- 76: acoustic matching layer
- 78: acoustic lens
- 80: filler layer
- 82: observation window
- 84: objective lens
- 86: solid-state imaging element
- 88: illumination window
- 90: cleaning nozzle
- 92: wiring cable
- 100: cable
- 102: outer coat
- 104: second cable bundle
- 106: resin layer
- 108: second shield layer
- 110: non-coaxial cable
- 112: signal wire
- 112a: conductor
- 112b: insulating layer
- 114: ground wire
- 116: first cable bundle
- 116a: distal end
- 118: first shield layer
- 130: fixing part
- 140: multiplexer
- 142: reception circuit
- 144: transmission circuit
- 146: A/D converter
- 148: ASIC
- 150: cine memory
- 151: memory controller
- 152: CPU
- 154: DSC
- 158: pulse generation circuit
- 160: phase matching unit
- 162: B mode image generation unit
- 164: PW mode image generation unit
- 166: CF mode image generation unit

What is claimed is:

1. An ultrasonography system comprising:
   an ultrasound transducer array in which a plurality of ultrasound transducers are arranged;
   a cable configured to be connected to the plurality of ultrasound transducers, and comprising a plurality of non-coaxial cables, and an outer coat configured to coat the plurality of non-coaxial cables,
wherein each of the plurality of non-coaxial cables comprises a first cable bundle having a plurality of signal wires and a plurality of ground wires, and a first shield layer configured to coat the first cable bundle;
a memory configured to store static capacitance data indicating static capacitance of each of the plurality of signal wires in the plurality of non-coaxial cables; and
a processor configured to correct transmission and reception sensitivity of the ultrasound transducers based on the static capacitance data stored in the memory so as to correct difference in static capacitance of the signal wires due to disposition of the signal wires.

2. The ultrasonography system according to claim 1, wherein the memory stores sensitivity data indicating sensitivity of each ultrasound transducer, and
the processor corrects the transmission and reception sensitivity of each ultrasound transducer based on the static capacitance data and the sensitivity data stored in the memory.

3. The ultrasonography system according to claim 1, wherein the processor drives each of the plurality of ultrasound transducers connected to the respective signal wires, via a substrate, having high static capacitance with a transmission signal having a higher voltage than the ultrasound transducer connected to the signal wire having low static capacitance.

4. The ultrasonography system according to claim 1, wherein the processor applies a higher gain value to a reception signal from the ultrasound transducer connected to the signal wire having high static capacitance than a reception signal from the ultrasound transducer connected to the signal wire having low static capacitance.

5. The ultrasonography system according to claim 1, wherein the processor applies a higher attenuation value to a reception signal from the ultrasound transducer connected to the signal wire having low static capacitance than a reception signal from the ultrasound transducer connected to the signal wire having high static capacitance.

6. The ultrasonography system according to claim 1, wherein, in the ultrasound transducer array, the ultrasound transducer connected to the signal wire having low static capacitance is disposed on a center side, and the ultrasound transducer connected to the signal wire having high static capacitance is disposed on an end portion side.

7. The ultrasonography system according to claim 1, wherein the processor sets a difference in transmission and reception sensitivity between the ultrasound transducers to be equal to or less than 2 dB.

* * * * *